United States Patent [19]

Young et al.

[11] Patent Number: 5,653,374
[45] Date of Patent: Aug. 5, 1997

[54] SELF-CONTAINED POWERED SURGICAL APPARATUS

[75] Inventors: Wayne P. Young, Brewster, N.Y.;
Daniel E. Alesi, Sherman, Conn.;
Kenneth E. Toso, Wilton, Conn.;
Henry Bolanos, East Norwalk, Conn.

[73] Assignee: United States Surgical Corporation, Norwalk, Conn.

[21] Appl. No.: 639,413

[22] Filed: Apr. 29, 1996

Related U.S. Application Data

[63] Continuation of Ser. No. 287,455, Aug. 5, 1994, abandoned.

[51] Int. Cl.$^6$ .................................................. A61B 17/068
[52] U.S. Cl. ...................... 227/176.1; 227/19; 227/178.1; 227/180.1
[58] Field of Search ............................. 227/175.1, 176.1, 227/178.1, 179.1, 180.1, 181.1, 19

[56] References Cited

U.S. PATENT DOCUMENTS

| | | |
|---|---|---|
| 1,881,250 | 10/1932 | Tomlinson . |
| 3,618,842 | 11/1971 | Bryan . |
| 3,815,476 | 6/1974 | Green et al. . |
| 3,952,748 | 4/1976 | Kaliher et al. . |
| 4,071,029 | 1/1978 | Richmond et al. . |
| 4,289,131 | 9/1981 | Mueller . |
| 4,334,539 | 6/1982 | Childs et al. . |
| 4,484,503 | 11/1984 | Sitte et al. . |
| 4,489,724 | 12/1984 | Arnegger . |
| 4,494,057 | 1/1985 | Hotta . |
| 4,520,817 | 6/1985 | Green . |
| 4,605,001 | 8/1986 | Rothfuss et al. . |
| 4,610,383 | 9/1986 | Rothfuss et al. . |
| 4,644,952 | 2/1987 | Patipa et al. . |
| 4,650,460 | 3/1987 | Roizenblatt . |
| 4,655,673 | 4/1987 | Hawkes . |
| 4,705,038 | 11/1987 | Sjostrom et al. . |
| 4,733,118 | 3/1988 | Mihalko . |
| 4,771,774 | 9/1988 | Simpson et al. . |
| 4,784,137 | 11/1988 | Kulik et al. . |
| 4,867,158 | 9/1989 | Sugg . |
| 4,887,599 | 12/1989 | Muller . |
| 4,936,845 | 6/1990 | Stevens . |
| 4,995,877 | 2/1991 | Ams et al. . |
| 5,040,715 | 8/1991 | Green et al. . |
| 5,059,203 | 10/1991 | Husted . |
| 5,071,430 | 12/1991 | de Salis et al. . |
| 5,133,359 | 7/1992 | Kedem . |
| 5,133,713 | 7/1992 | Huang et al. . |
| 5,133,729 | 7/1992 | Sjostrom . |

(List continued on next page.)

FOREIGN PATENT DOCUMENTS

| | | |
|---|---|---|
| 0156774 | 3/1985 | European Pat. Off. . |
| 0216532 | 8/1986 | European Pat. Off. . |
| 0536903 | 9/1992 | European Pat. Off. . |
| 0539762 | 10/1992 | European Pat. Off. . |
| 0552050 | 7/1993 | European Pat. Off. . |
| 0593920 | 9/1993 | European Pat. Off. . |
| 0598579 | 11/1993 | European Pat. Off. . |
| 0621006 | 3/1994 | European Pat. Off. . |
| 0634144 | 1/1995 | European Pat. Off. . |
| 2660851 | 10/1991 | France . |
| 2903159 | 7/1980 | Germany . |
| 3114135 | 10/1982 | Germany . |
| 4213426 | 10/1992 | Germany . |
| 51149985 | 1/1950 | Japan . |
| 659146 | 4/1979 | U.S.S.R. . |
| 9308754 | 5/1993 | WIPO . |
| 9314706 | 8/1993 | WIPO . |

*Primary Examiner*—Scott A. Smith

[57] ABSTRACT

A self-contained powered surgical stapling device is provided which includes an elongate body. A fastener applying assembly is operatively associated with a distal end of the elongate body and includes a cartridge housing a plurality of staples and an anvil actuable to move between an open position and a closed position. A motor assembly is disposed within the elongate body for driving an actuation assembly configured to translate through the fastener applying assembly to progressively close the anvil and sequentially eject staples from the cartridge.

22 Claims, 10 Drawing Sheets

U.S. PATENT DOCUMENTS

| | | |
|---|---|---|
| 5,170,925 | 12/1992 | Madden et al. . |
| 5,192,292 | 3/1993 | Cezana et al. . |
| 5,201,750 | 4/1993 | Hocherl et al. . |
| 5,207,697 | 5/1993 | Carusillo et al. . |
| 5,221,279 | 6/1993 | Cook et al. . |
| 5,237,884 | 8/1993 | Seto . |
| 5,249,583 | 10/1993 | Mallaby . |
| 5,258,007 | 11/1993 | Spetzler et al. . |
| 5,261,877 | 11/1993 | Fine et al. . |
| 5,268,622 | 12/1993 | Philipp . |
| 5,289,963 | 3/1994 | McGarry et al. . |
| 5,312,023 | 5/1994 | Green et al. . |
| 5,318,221 | 6/1994 | Green et al. . |
| 5,326,013 | 7/1994 | Green et al. . |
| 5,467,911 | 11/1995 | Tsuruta et al. . |

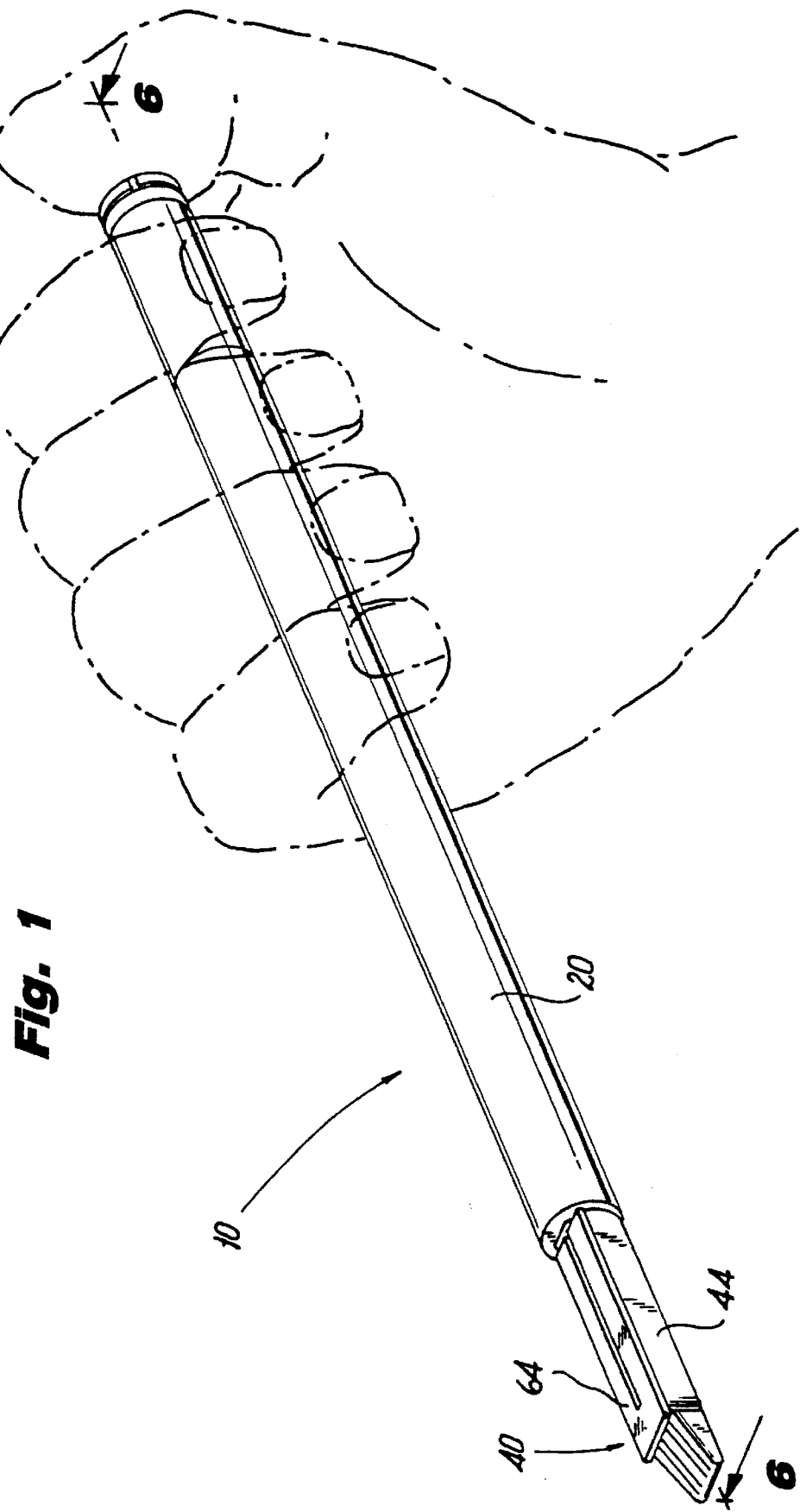

SELF-CONTAINED POWERED SURGICAL APPARATUS

This is a continuation of U.S. application Ser. No. 08/287,455 filed Aug. 5, 1994, now abandoned.

BACKGROUND

1. Technical Field

A self-contained powered surgical stapling apparatus is provided for sequentially applying a plurality of surgical fasteners to body tissue and optionally incising the fastened tissue.

2. Background of Related Art

Surgical devices wherein tissue is first gasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can include two elongated members which are respectively used to capture or clamp tissue. Typically, one of the members carries a disposable cartridge which houses a plurality of staples arranged in at least two lateral rows while the other member includes an anvil which defines a surface for forming the staple legs as the fasteners are driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. No. 3,079,606 to Bobroy et at. and U.S. Pat. No. 3,490,675 to Green.

A later stapler disclosed in U.S. Pat. No. 3,499,591 to Green applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples.

Each of the instruments described above were designed for use in conventional surgical procedures wherein surgeons have direct manual access to the operative site. However, in endoscopic or laparoscopic procedures, surgery is performed through a small incision or through narrow a cannula inserted through small entrance wounds in the skin. In order to address the specific needs of endoscopic and/or laparoscopic surgical procedures, an endoscopic surgical stapling apparatus has been developed and is disclosed in U.S. Pat. No. 5,040,715. This apparatus is well suited for such procedures and includes a fastener applying assembly having an anvil and a staple cartridge provided at the distal end of an endoscopic body portion which permits the instrument to be inserted into a cannula and be remotely operated by the surgeon through manipulation of a proximal handle mechanism.

The instruments discussed above all require some degree of manually applied force in order to clamp, fasten and/or cut tissue. Surgeons have thus recognized the benefits of using self-powered instruments that are actuable with only a limited degree of physical force. Self-powered surgical instruments have been provided to serve these needs and include both gas powered surgical staplers, as shown, for example, in U.S. Pat. No. 5,312,023, and electrically powered surgical instruments as described in U.S. Pat. Nos. 4,635,638 and 5,258,007, and European Pat. Appln. No. 0 552 050. In general, prior art electrically powered surgical instruments have been driven by external power sources. The instruments were connected to the power sources by conductive cables. Such cables could, however, become entangled during a surgical procedure, thereby complicating the operation.

It would be beneficial to provide a self-contained powered surgical apparatus for applying a plurality of surgical staples to body tissue and concomitantly incising the stapled tissue. Such an apparatus should be compact, lightweight and easy to manufacture. Currently, surgical instruments are designed for use in either open, i.e. invasive procedures, or endoscopic/laparoscopic procedures. As noted above, endoscopic instruments require elongate shafts to access remote surgical sites. Conventional surgical instruments are not constructed in this manner. It would be advantageous to provide a powered surgical instrument which can be readily adapted for use in both conventional and laparoscopic procedures.

SUMMARY

A self-contained powered surgical apparatus for applying a plurality of surgical fasteners to body tissue is provided. The apparatus includes an elongate instrument body defining a longitudinal axis, a cartridge assembly housing a plurality of surgical fasteners, and an anvil member mounted adjacent the cartridge assembly and configured for movement with respect thereto between an open and a closed position.

The apparatus further includes a motor assembly disposed within the elongate instrument body, an actuating assembly driven by the motor assembly for effectuating progressive closure of the anvil and sequential ejection of the surgical fasteners and a power source disposed within the body for energizing the motor assembly. Preferably, the actuating assembly includes a drive member which is threadably associated with an axial drive screw that is driven by the motor assembly.

In a preferred embodiment, the actuating assembly includes a first camming mechanism configured to move the anvil member into a closed position to clamp tissue, and a second camming mechanism configured to sequentially eject fasteners from the cartridge as it translates therethrough. A tissue cutting member is preferably associated with the actuating assembly for translating through the cartridge assembly to incise the stapled body tissue. A control for the motor assembly to operate the powered surgical apparatus preferably includes first and second control buttons for effecting distal and proximal movement of the actuating assembly.

In one embodiment, the powered surgical apparatus includes an elongate shaft configured to engage with a proximal end of the main instrument body to facilitate utilization of the apparatus during an endoscopic procedure. Preferably, the extension shaft interacts with the motor control buttons at the proximal end of the main instrument body to operate the apparatus from a location remote from the surgical site.

In another embodiment, the powered surgical apparatus is intended to be employed during a laparoscopic procedure by providing a mechanical hand which is configured to extend into the abdominal cavity through a cannula and be remotely manipulated to actuate the apparatus.

Further features of the powered surgical apparatus will become more readily apparent to those skilled in the art from the following detailed description of the invention taken in conjunction with the drawings.

BRIEF DESCRIPTION OF THE DRAWINGS

Various embodiments of the powered surgical apparatus will be described hereinbelow with reference to the drawings wherein:

FIG. 1 is a perspective view of a powered stapling device constructed in accordance with a preferred embodiment;

DETAILED DESCRIPTION OF PREFERRED EMBODIMENTS

Figure 2A:
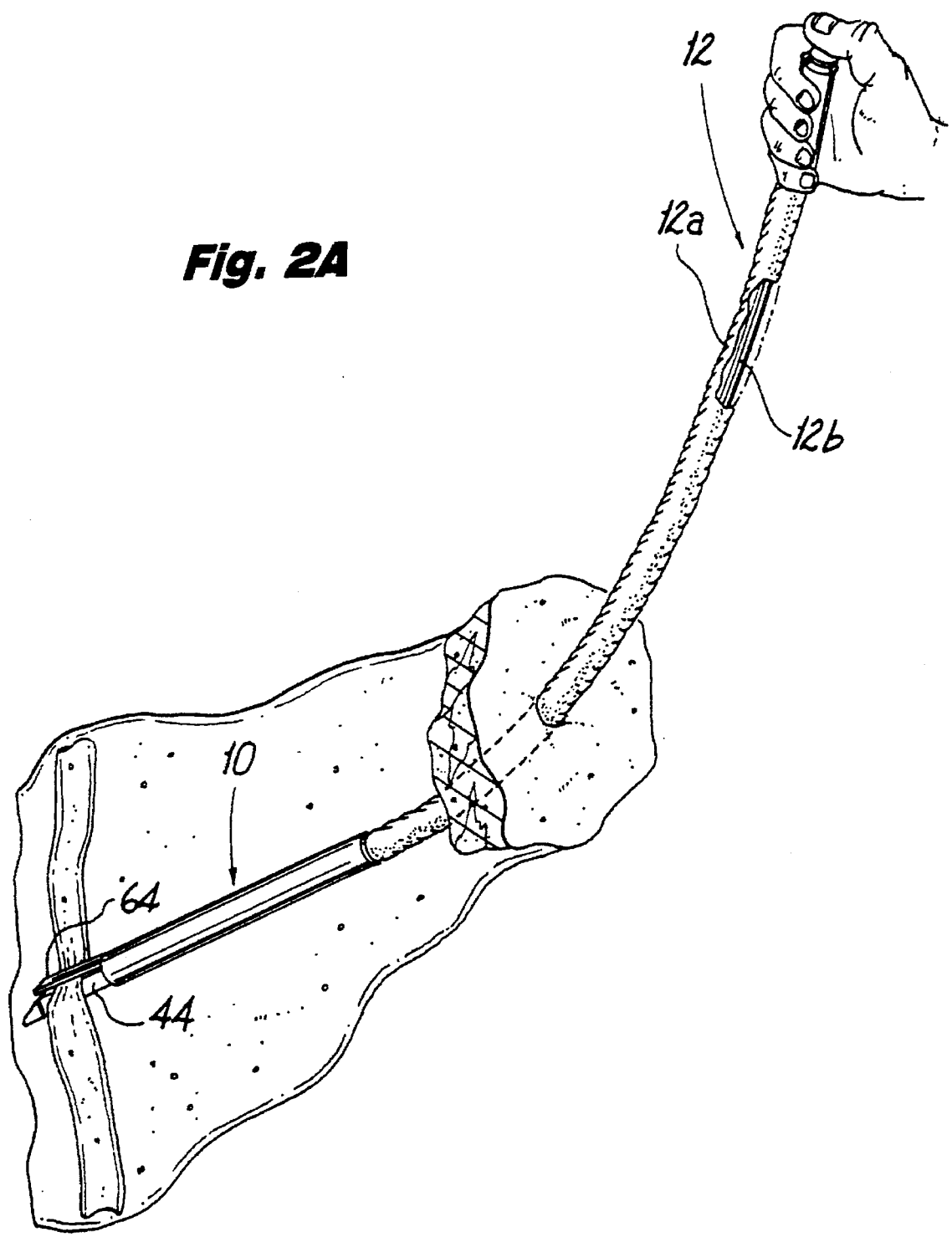
FIG. 2A is an illustration depicting the powered stapling device of FIG. 1 with a flexible extension shaft attached thereto in use during a laparoscopic procedure.

In the drawings and in the description which follows, the term "proximal", as is traditional, will refer to the end of the apparatus which is closest to the operator, while the term "distal" will refer to the end of the apparatus which is furthest from the operator.

The apparatus shall be discussed in terms of both conventional and endoscopic procedures. However, use herein of terms such as "endoscopic", "endoscopically", and "endoscopic portion", among others, should not be construed to limit the present apparatus for use only in conjunction with an endoscopic tube. To the contrary, it is believed that the present apparatus may find use in procedures wherein access is limited to a small incision including but not limited to arthroscopic and/or laparoscopic procedures.

Referring now to the drawings wherein like reference numerals identify similar structural elements of the apparatus, there is illustrated in FIG. 1 a self-contained powered surgical stapler constructed in accordance with a preferred embodiment and designated generally by reference numeral 10.

Figure 2B:
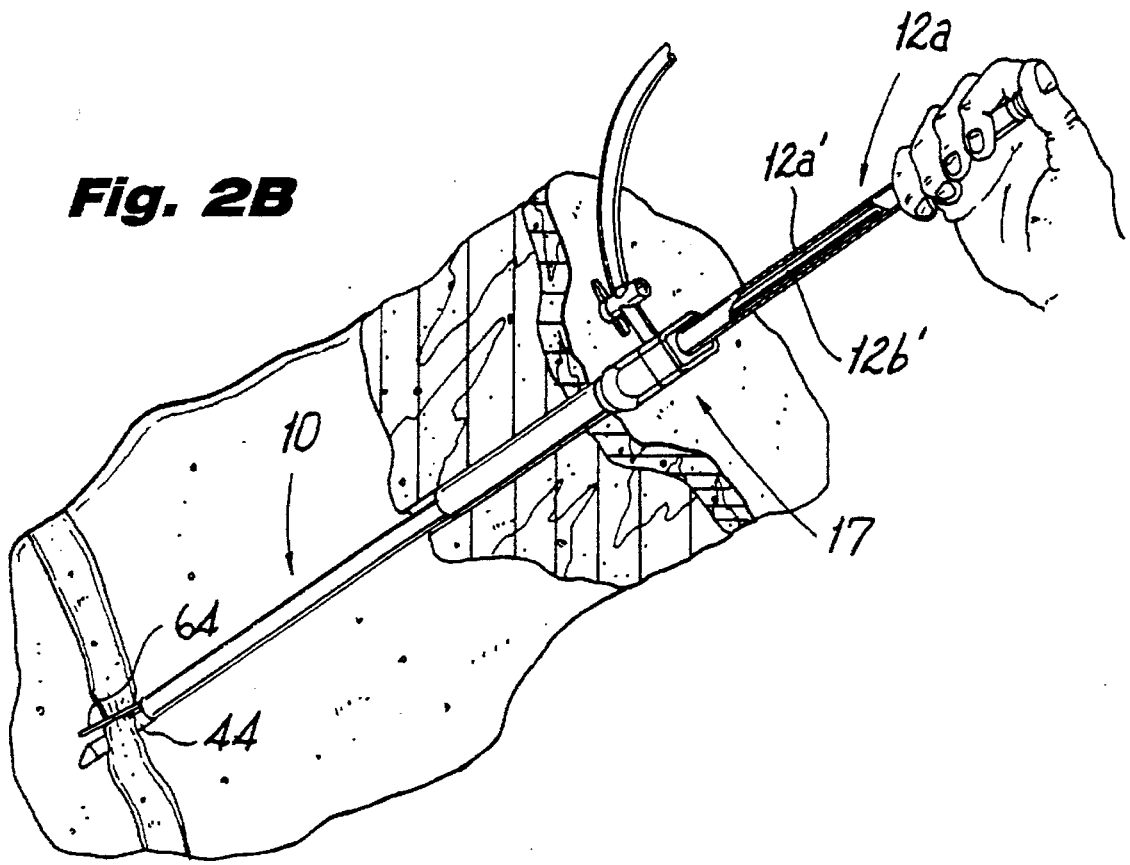
FIG. 2B is an illustration depicting the powered stapling device of FIG. 1 with a rigid extension shaft attached thereto in use during a laparoscopic procedure.

Referring to FIG. 1, powered surgical apparatus 10 is configured for use as a hand-held device for applying a plurality of surgical staples to tubular vessels and body tissue during conventional invasive surgical procedures. By way of example only, surgical apparatus 10 may have a length measuring from about 5.0 inches to about 7.0 inches, and an outer diameter of about 0.450 inches to about 0.500 inches. Preferably, the length of surgical apparatus 10 is between 6.0 inches and 6.5 inches, while the preferred diameter is between 0.470 inches and 0.480 inches. Clearly, other dimensions are contemplated. In one embodiment, surgical apparatus 10 is also adapted for use in endoscopic procedures through remote actuation from a location outside the patient's body, as shown in FIGS. 2A and 2B. This is achieved by providing an elongated extension shaft 12 which attaches to the proximal end of surgical apparatus 10 by commonly known connective methods such as snap fit. Extension shaft 12 is preferably dimensioned and configured for insertion through a cannula or trocar device and has a length measuring from about 10.0 inches to about 17.0 inches. A flexible shaft 12 or rigid shaft 12' can be utilized.

Figure 3:
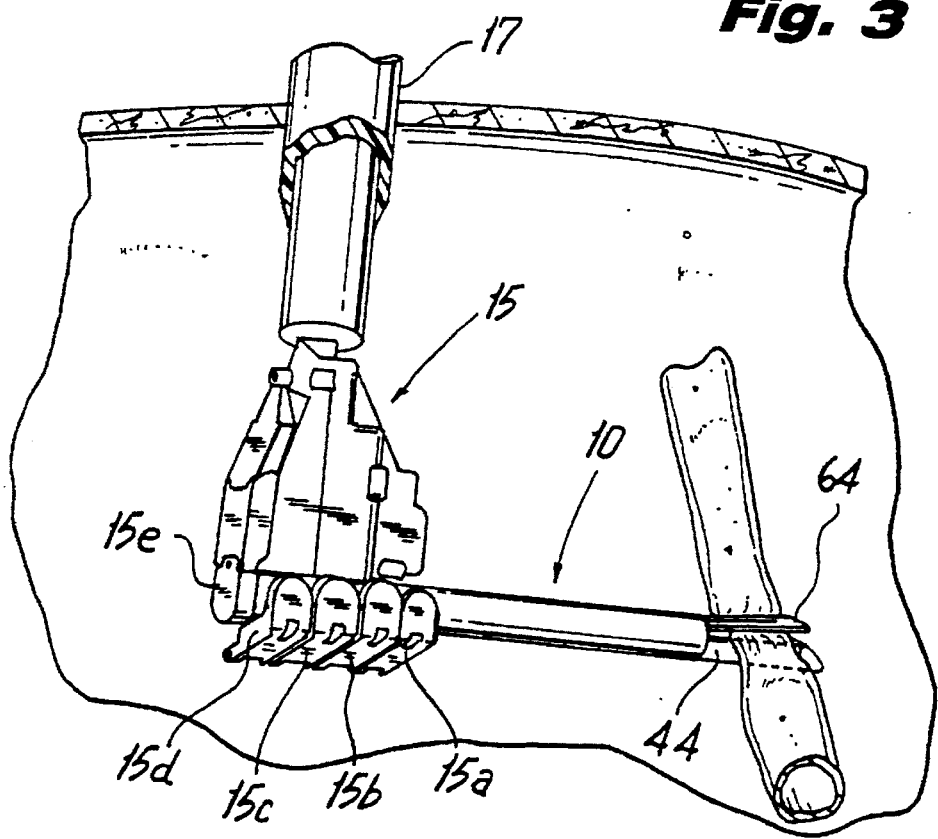
FIG. 3 is an illustration depicting a mechanical hand operating the powered stapling device of FIG. 1 during a laparoscopic procedure.

Referring to FIG. 3, in another embodiment, surgical apparatus 10 is intended to be operated by a mechanical hand 15 which is configured to extend through trocar device 17 during a laparoscopic surgical procedure. Mechanical hand 15 includes four articulated fingers 15a–15d and an opposable thumb 15e which are hinged together to enable relative movement between a constricted position wherein the forehand and fingers are drawn together into a narrowed formation to facilitate their extension through trocar 17 and a relaxed position wherein the forehand and fingers are deployed into a spread position to perform dexterous tasks such as operating surgical apparatus 10 by actuating a switch provided on the apparatus.

Figure 4:
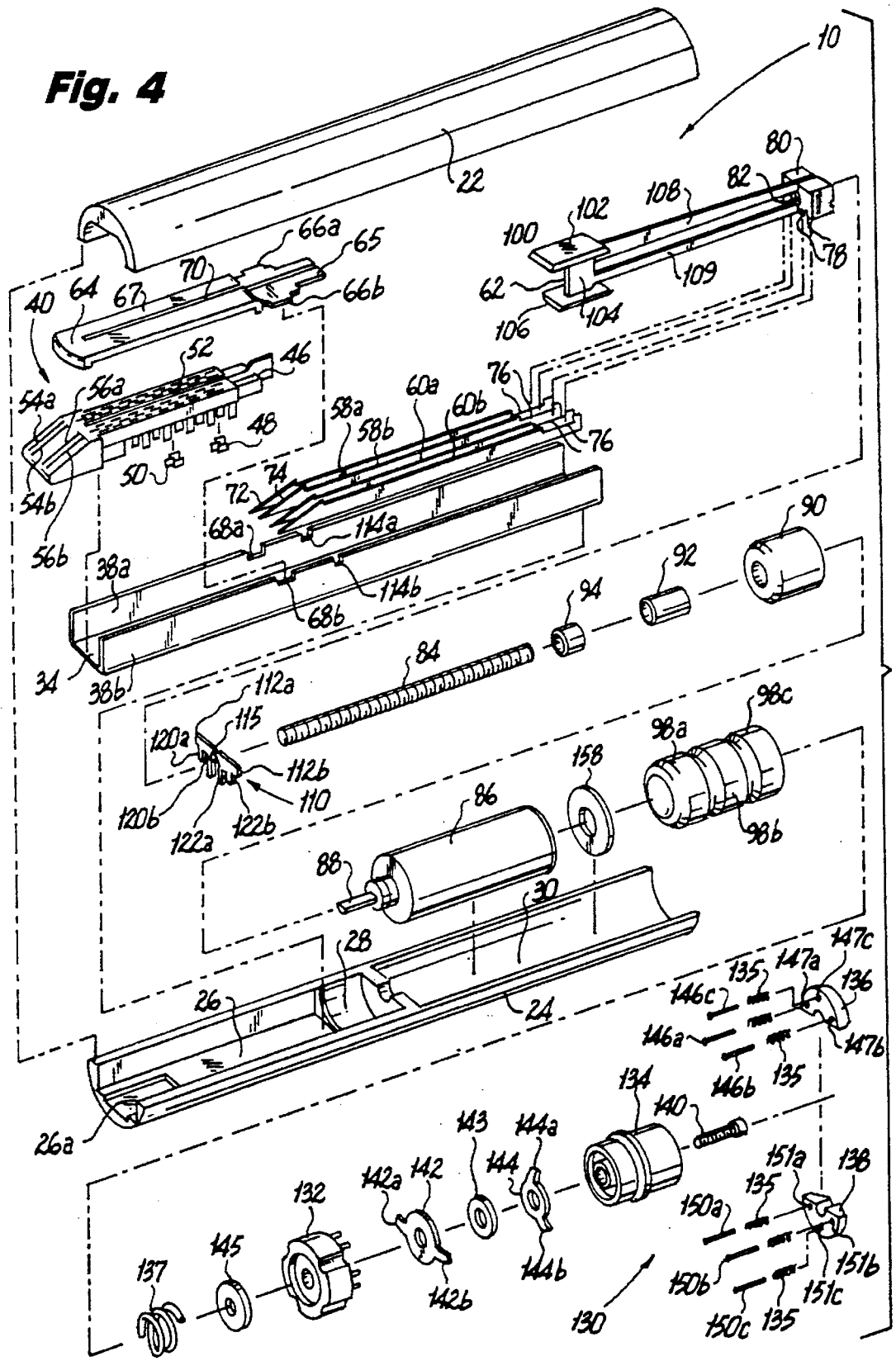
FIG. 4 is an exploded perspective view of the powered stapling device of FIG. 1.

Referring to FIG. 4, surgical apparatus 10 includes an elongate body 20 including complimentary body sections 22 and 24 which define a series of internal chambers for housing and supporting various mechanical components of apparatus 10. The internal chambers defined within body sections 22 and 24 include distal chamber 26, medial chamber 28, and proximal chamber 30.

The components housed within body sections 22 and 24 of surgical apparatus 10 include an elongate housing channel 32 having a base 34 and opposed upstanding channel walls 38a and 38b. Housing channel 32 is maintained within the distal chamber 26 of body 20 and is configured to support the assembly 40 and the actuating assembly 42.

The assembly 40 includes an elongate staple cartridge 44 having a plurality of transverse slots 46 each configured to support a respective staple 48 and staple pusher 50. Cartridge 44 is also provided with five spaced apart longitudinal slots including a central slot 52 and lateral slot pairs 54a, 54b and 56a, 56b. The lateral slot pairs 54a, 54b and 56a, 56b serve to accommodate longitudinal translation of the elongate camming bars 58a, 58b and 60a, 60b of actuating assembly 42 while the central slot 52 serves to accommodate longitudinal translation of a cutting blade 62. Actuating assembly 42 and the components associated therewith will be described in greater detail hereinbelow.

Assembly 40 further includes an elongate anvil 64 which defines an interior fastener forming surface 65 against which staples are driven when ejected from cartridge 44 by the actuating assembly 42. A pair of outwardly depending wings 66a and 66b are formed adjacent the proximal end of anvil 64 for engaging a pair of correspondingly positioned reception slots 68a and 68b formed in the opposed upstanding channel walls 38a and 38b of housing channel 32. The engagement of wings 66a and 66b within slots 68a and 68b facilitates pivotal movement of anvil 64 with respect to cartridge 44. A longitudinal slot 70 extends along a substantial portion of the length of anvil 64 to accommodate the longitudinal translation of cutting blade 62 and the portion of actuating assembly 42 which supports the cutting blade. Similarly, a longitudinal slot 75 is formed in the base 34 of housing channel 32 (see FIG. 6). The orientation and length of slots 70 and 75 correspond substantially to that of the central slot 52 provided in cartridge 44.

A spring 65 extends from the proximal end of anvil 64 and is attached to body section 22 (or alternatively base 34) to bias the anvil towards the cartridge 44. Thus, in use, as tissue is positioned between the anvil and cartridge, the anvil is forced away from the cartridge by the tissue. Actuation of the actuating assembly (discussed below) forces anvil 64 into closer cooperative alignment with cartridge 44 to more firmly and progressively clamp the tissue. In an alternate embodiment, the anvil 64 is biased to an open position, i.e. biased away from cartridge 44, by, for example, a pair of springs positioned at a proximal end of the anvil between the anvil and cartridge 44. It is also contemplated that the anvil can be connected for free movement with respect to the cartridge without a spring bias.

As best seen in FIG. 4, actuating assembly 42 includes two pairs of elongate camming bars 58a, 58b and 60a, 60b. The camming bars serve to sequentially eject staples 48 from cartridge 44 through interaction with staple pushers 50. In particular, each of the elongate camming bars includes a distal head portion 72 having an angled camming surface 74. Camming surface 74 is configured to contact staple pushers 50 and drive the staple pushers in a direction transverse to the longitudinal axis of cartridge 44, thereby urging the staples from cartridge 44. An engagement notch 76 is formed adjacent the proximal end of each of the camming bars for engaging corresponding grooves 78 provided in drive member 80.

Figure 9:
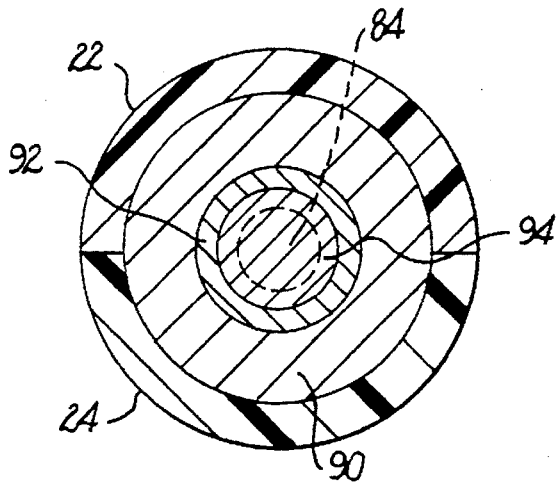
FIG. 9 is a cross-sectional view taken along line 9—9 of FIG. 6 illustrating the drive shaft of the motor assembly.
Figure 10:
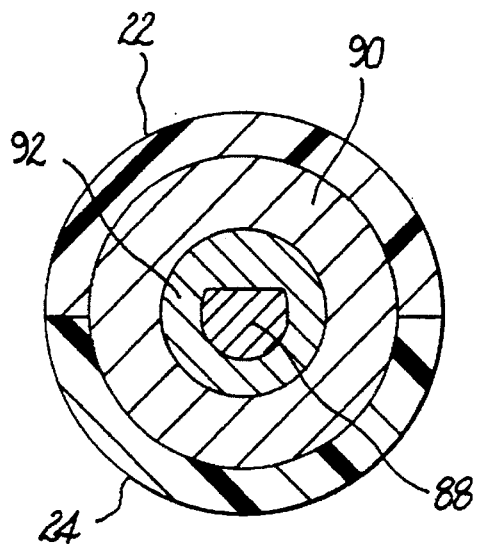
FIG. 10 is a cross-sectional view taken along line 10—10 of FIG. 6 illustrating the interaction between the drive shaft of the motor assembly and the axial drive screw.

Drive member 80 includes a threaded bore 82 for operatively engaging an axial drive screw 84. Drive screw 84 is driven by a motor assembly 86 and is connected to the drive shaft 88 of motor assembly 86 by a supporting hub assembly which includes an outer support hub 90, an intermediate support hub 92, and an inner engagement hub 94 (see FIG. 9). Engagement hub 94 is fastened to the proximal end of drive screw 84 and is engaged within the intermediate support hub 92. As shown in FIG. 10, drive shaft 88 is keyed into the opposed end of support hub 92. Support hub 92 is coaxially disposed within outer support hub 90 which is maintained with the medial chamber 28 of elongate body 20. Motor assembly 86 and the power cells 98a–98c which supply energy thereto are maintained with the proximal chamber 30 of elongate body 20. A transfer plate 158 is disposed between the distal-most power cell 98a and the proximal end of motor assembly 86 for transferring energy from the power cell to the motor assembly.

Actuating assembly 42 further includes a camming beam 100 for effectuating the progressive closure of anvil 64 to clamp body tissue disposed between fastener forming surface 65 of anvil 64 and the tissue contacting surface 45 of staple cartridge 44. Camming beam 100 includes an upper beam portion 102, a central web portion 104, and a lower beam portion 106. Central web portion 104 supports cutting blade 62. Upper and lower beam extensions 108 and 109 extend proximally from central web portion 104 to engage drive member 80. As shown, the upper and lower beam portions 102, 106 are substantially planar. Thus, the mechanism for clamping the anvil (camming beam 100) and the mechanism for firing the staples from the cartridge (camming bars 58a, 58b and 60a, 60b) are directly connected to drive member 80. In use, the upper beam portion 102 of camming beam 100 progressively contacts the outer surface 67 of anvil 64 to effect progressive anvil closure. The central web 104 translates through slots 52, 70, and 75, and the lower beam portion 106 translates along the outer surface 35 of the base 34 of housing channel 32 to maintain anvil closure during a stapling procedure.

Figure 8:
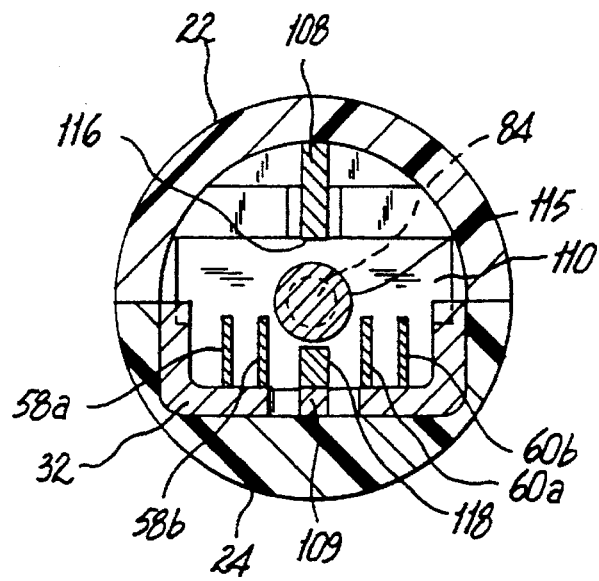
FIG. 8 is a cross-sectional view taken along line 8—8 of FIG. 6 illustrating the actuating assembly.

Referring to FIG. 8 in conjunction with FIG. 4, a support gate 110 is mounted intermediate housing channel 32 which has an aperture 115 for supporting the distal end portion of axial drive screw 84. As best seen in FIG. 4, support gate 110 includes a pair of opposed winglets 112a and 112b for engaging corresponding reception slots 114a and 114b in the opposed channel walls 38a and 38b of housing channel 32. Upper and lower grooves 116 and 118 are formed in support gate 110 to accommodate the translation of the upper and lower beam extensions 108 and 109. Lateral slot pairs 120a, 120b and 122a, 122b are provided in support gate 110 to accommodate the translation of camming bar pairs 58a, 58b and 60a, 60b.

Surgical apparatus 10 further includes a switching assembly 130 for selectively controlling the operation of motor assembly 86. Switching assembly 130 includes distal and proximal switch housings 132 and 134, and right and left spring biased actuation buttons 136 and 138. A plurality of coiled compression springs 135 bias actuation buttons 136 and 138 in a proximal direction. Switch housings 132 and 134 are mounted to one another and fastened to the proximal end of surgical apparatus 10 by a threaded connector 140, and are operatively separated from one another by a distal insulating ring 141, a distal contact plate 142, a medial insulating ring 143, and a proximal contact plate 144. A distal contact ring 145 is disposed between distal switch housing 132 and spring 137.

Distal contact plate 142 includes a pair of opposed upturned contact tabs 142a and 142b, and proximal contact plate 144 includes a pair of opposed upturned contact tabs 144a and 144b which are positioned 60° out of phase with tabs 142a and 142b. Each actuation button has associated therewith three contact pins, two of which interact with contact plates 142 and 144 to control the relative movement of drive screw 84. In particular, actuation button 136 includes two long pins 146a and 146b and one short pin 146c. Short pin 146c is seated within a central reception port 147c, while long pins 146a and 146b are seated within lateral reception ports 147a and 147b.

Long pin 146a and short pin 146c are positioned to selectively engage contact tabs 142a and 144b respectively, while long pin 146b remains free from electrical contact. Similarly, actuation button 138 includes long pins 150a and 150b, and short pin 150c. Short pin 150c is seated within a central reception port 151c, while long pins 150a and 150b are seated within lateral reception ports 151a and 151b. Long pin 150b and short pin 150c are positioned to selectively engage contact tabs 142b and 144b respectively, while long pin 150a remains free from electrical contact.

Figure 5:
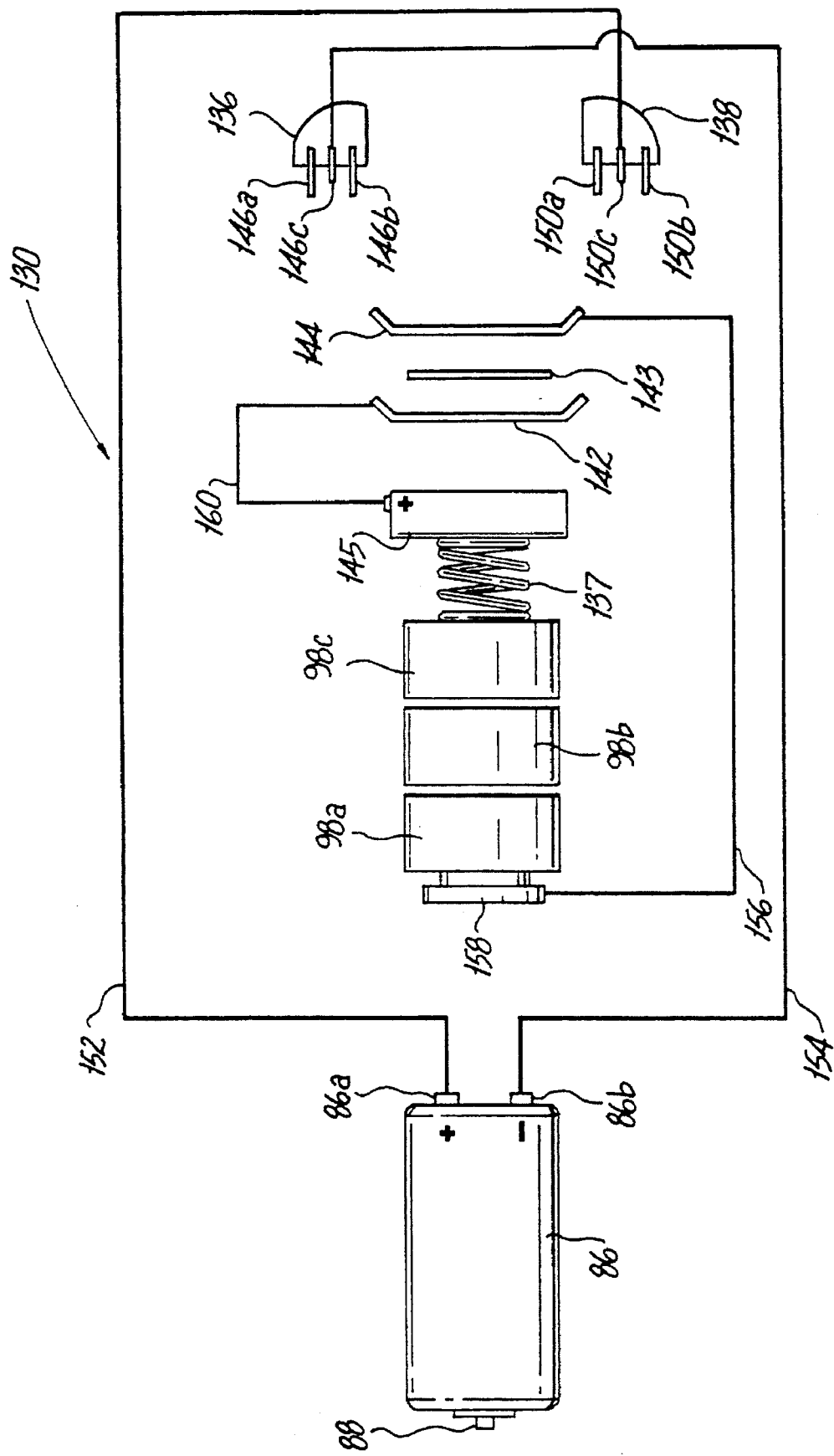
FIG. 5 is a schematic representation of the switching mechanism for controlling the operation of the motor assembly.

The wiring configuration of switching assembly 130 is illustrated in FIG. 5 and includes motor line 152 which interconnects the positive terminal 86a of motor assembly 86 to contact pins 146a and 150c, and a motor line 154 which interconnects the negative terminal 86b of motor assembly 86 to contact pins 146c and 150b. In addition, a transmission line 156 extends between battery transfer plate 158 and contact plate 144, and a transmission line 160 interconnects contact plate 142 and contact ting 145.

In use, when actuation button 138 is depressed, long pin 150b contacts tab 142b of distal contact plate 142 and short pin 150c contacts tab 144b of proximal contact plate 144. Thus, the positive terminals of power cells 98a–98c will be connected to the negative terminal 86b of motor assembly 86 and the negative terminals of power cells 98a–98c will be connected to the positive terminal 86a of motor assembly 86, causing drive shaft 88 to rotate in a clockwise direction to move drive member 80 distally. When actuation button 136 is depressed, long pin 146a contacts tab 142a of distal contract plate 142 and short pin 146c contacts tab 144a proximal contact plate 144. Thus, the positive terminals of power cells 98a–98c will be connected to the positive terminal 86a of motor assembly 86 and the negative terminals of power cells 98a–98c will be connected to the negative terminal 86b of motor assembly 86, causing drive shaft 88 to rotate in a counter-clockwise direction to move the axial drive member 80 in a proximal direction. It is also envisioned that a single actuator button can be provided which will be actuable to operate an axial drive screw having a reverse thread formed therein. The reverse thread will cause a distally translating drive screw to automatically translate in a proximal direction at the conclusion of a fastener forming stroke.

As discussed briefly hereinabove, surgical apparatus 10 is preferably designed for insertion through a trocar or cannula device to apply surgical staples to body tissue located within a body cavity while being actuable remote from the surgical site. Shaft 12 includes elongate transmission members 12a and 12b (or 12a' and 12b') for effectuating remote actuation of switching assembly 130 (see FIGS. 2A and 2B). Transmission members 12a and 12b (or 12a and 12b) may include a pair of substantially rigid rods for transmitting a mechanical signal to actuation buttons 136 and 138, or, in the alternative, the transmission members may include transmission cables for directing an electrical signal to switching assembly 130. In either instance, the shaft would include two actuation buttons to respectively actuate buttons 136 and 138 and cause the rotation of drive screw 84 in opposed directions.

Figure 6:
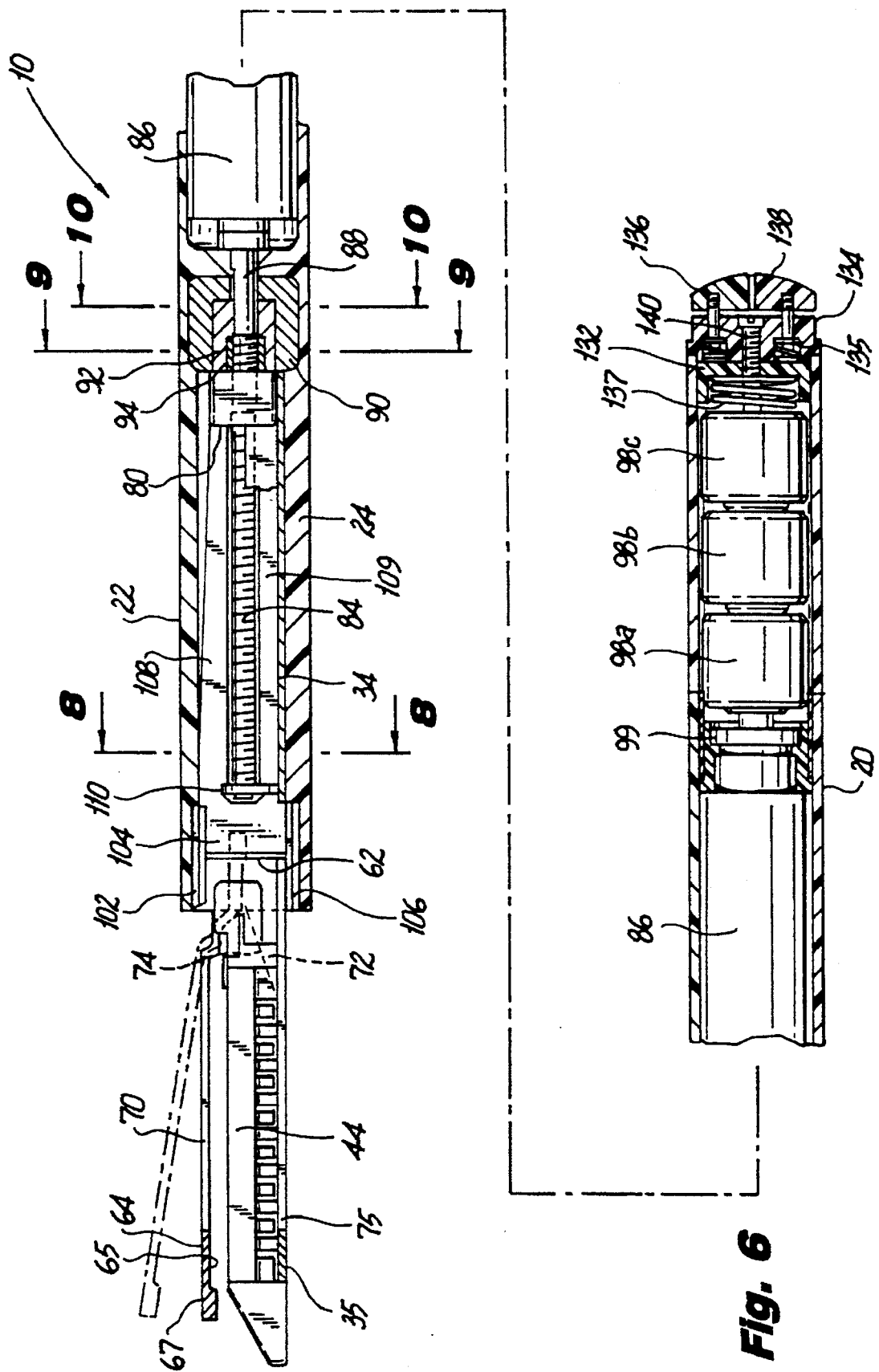
FIG. 6 is a side elevational view in cross-section taken along line 6—6 of FIG. 1 illustrating the relative position of the internal components of the powered stapling device prior to actuation.
Figure 7:
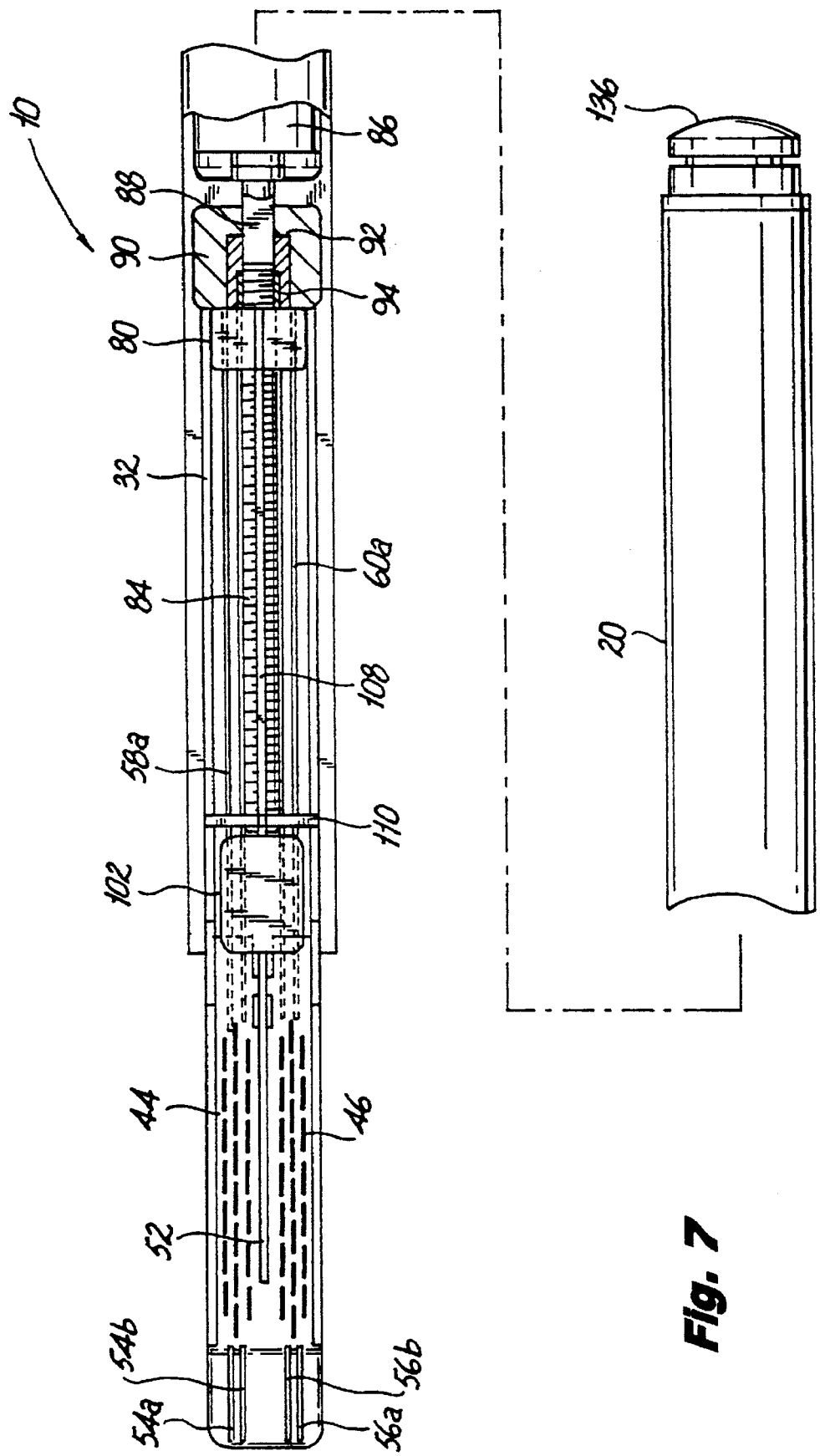
FIG. 7 is a top plan view in cross-section illustrating the relative position of the internal components of the powered stapling device prior to actuation.

Referring now to FIGS. 6 and 7, prior to operating the surgical stapling device 10, the anvil 64 is disposed in a free-movement position to facilitate the capture of body tissue (or spring biased to a closed or an open position as in the aforementioned alternate embodiments). Movement of anvil 64 is accommodated by the pivotal engagement of anvil wings 66a and 66b in reception slots 68a and 68b. The pivotal movement of anvil 64 is best seen in FIG. 6. Prior to actuation, camming beam 100 is maintained within a support seat 26a defined in the distal chamber 26 of instrument body 20. At such a time, the upper beam portion 102 is out of contact with the outer surface 67 of anvil 64 permitting the pivotal movement thereof. Also at this time, the distal head portion 72 of each of the camming bars 58a, 58b and 60a, 60b is disposed proximal to and out of contact with the proximal-most staple pushers 50 in cartridge 44.

Figure 11:
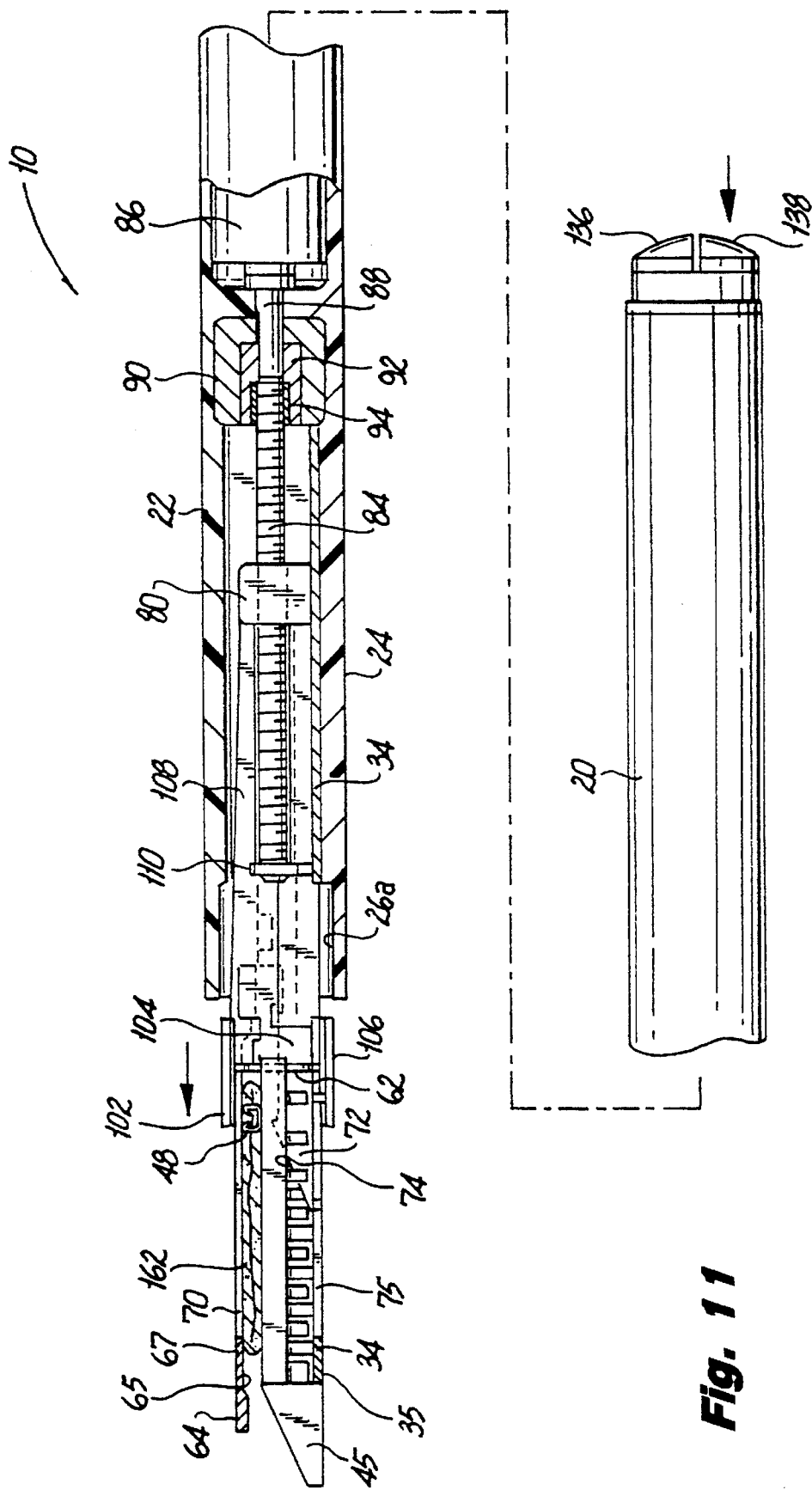
FIG. 11 is a side elevational view in cross-section illustrating the relative position of the internal components of the powered stapling device during a stapling operation.
Figure 12:
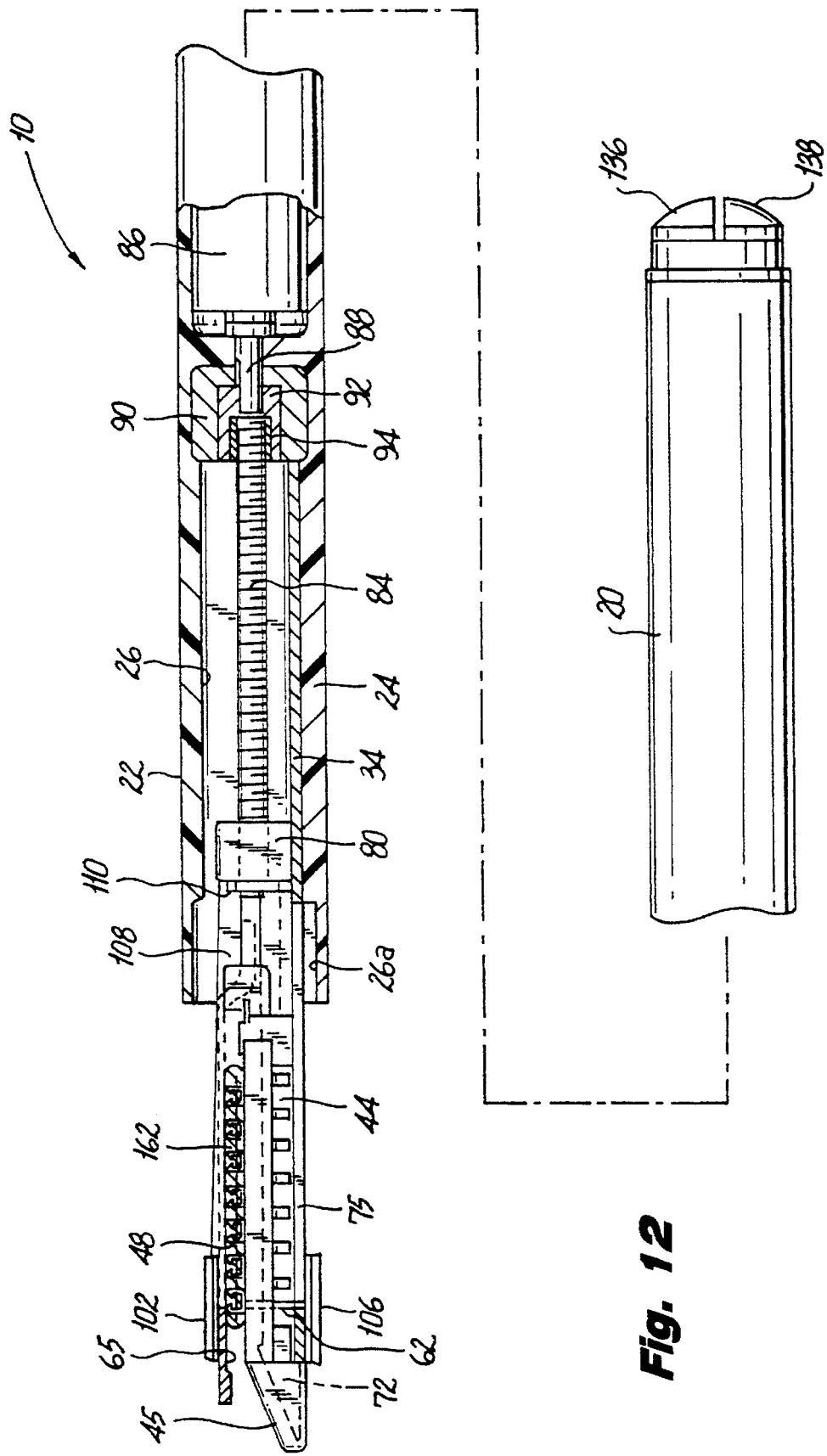
FIG. 12 is a side elevational view in cross-section illustrating the relative position of the internal components of the powered stapling device at the completion of a stapling operation.

Upon actuation, i.e. when actuation button 136 is depressed, motor assembly 86 is energized and drive shaft 88 rotates axial drive screw 84, causing drive member 80 to translate in a distal direction. As best seen in FIG. 11, as drive member 80 translates distally, the upper beam portion 102 of camming beam 100 progressively urges anvil 64 toward cartridge 44 to clamp body tissue 165 therebetween. Concomitantly, the camming surface 74 on the distal head portion 72 of each of the camming bars of actuation assembly 42 interacts with staple pushers 50 to sequentially eject surgical staples 48 from cartridge 44.

Staples ejected from cartridge 44 are driven through body tissue 165 and formed against the inner fastener forming surface 65 of anvil 64. As the rows of staples are placed in body tissue 165, cutting blade 62, which travels behind the distal head portion 72 of each of the camming bars of actuation assembly 42, cuts the stapled body tissue, forming an incision between the staple rows.

Continued actuation of motor assembly 86 effects distal translation of drive member 80 until the drive member contacts support gate 110. At such a time, camming beam 100 is disposed at the distal end of fastener applying assembly 40 and the distal head 70 of each of the camming bars is disposed within the distal portion 45 of staple cartridge 44. Following the stapling operation, depression of actuation button 138 causes drive member 80 to translate proximally, drawing therewith camming beam 100 and camming bars 58a, 58b and 60a, 60b to their proximal-most position (FIG. 6).

It is also contemplated that the staple cartridge 44 can be removable so that once actuation assembly 42 has returned to its proximal-most position after firing the fasteners, staple cartridge 44 can be removed and replaced with a loaded staple cartridge and actuation button 136 can be depressed again to fire the stapling apparatus.

Although the apparatus has been described with respect to preferred embodiments, it will be readily apparent to those having ordinary skill in the art to which it appertains that changes and modifications may be made thereto without departing from the spirit or scope of the appended claims.

What is claimed is:

1. A self-contained powered surgical apparatus for applying surgical fasteners to body tissue comprising:

a) an elongate body defining a longitudinal axis;

b) a cartridge supported by said elongate body and housing a plurality of surgical fasteners and having a tissue engaging surface thereon;

c) an anvil member having a fastener forming surface thereon, the anvil member mounted adjacent the cartridge and configured for relative movement between an open position wherein said fastener forming surface is spaced from said tissue engaging surface and a closed position wherein said fastener forming surface is in close cooperative alignment with said tissue engaging surface;

d) a motor assembly disposed within the elongate body;

e) a power source disposed within the elongate body for energizing the motor assembly; and f) an actuating assembly including a longitudinally translating drive member driven by the motor assembly and first and second camming mechanisms driven by the drive member; and g) wherein movement of the drive member in a longitudinal direction initially causes the first camming mechanism to effect relative movement of the anvil member and the cartridge and subsequently causes the second camming mechanism to effect sequential ejection of a plurality of surgical fasteners from the cartridge.

2. A powered surgical apparatus as recited in claim 1, wherein the drive member is threadably associated with an axial drive screw which is driven by the motor assembly.

3. A powered surgical apparatus as recited in claim 1, further comprising a tissue cutting member operatively associated with the actuating assembly for incising tissue as a plurality of surgical fasteners are ejected from the cartridge.

4. A powered surgical apparatus as recited in claim 1, further comprising an actuator for selectively controlling the motor assembly to operate the apparatus.

5. A powered surgical apparatus as recited in claim 4, wherein the actuator includes a first actuator button for effecting distal translation of the actuating assembly and a second actuator button for effecting proximal translation of the actuating assembly.

6. A powered surgical apparatus as recited in claim 4, further comprising an elongate extension member configured to engage a proximal end of the elongate body to facilitate utilization of said apparatus during an endoscopic surgical procedure.

7. A powered surgical apparatus as recited in claim 6, wherein the elongate extension member includes a pair of rods or cables for interacting with the actuator to effectuate remote operation of the apparatus.

8. A powered surgical apparatus as recited in claim 7, wherein the actuator and extension member each include a pair of actuator buttons.

9. A powered surgical apparatus as recited in claim 1, wherein the apparatus has a substantially uniform diameter along the entire length thereof.

10. A powered surgical apparatus as recited in claim 1, wherein the apparatus has an operative length of less than 7.0 inches.

11. A powered surgical apparatus as recited in claim 1, wherein the anvil member is biased to the open position.

12. A powered surgical apparatus as recited in claim 1, wherein the actuating assembly progressively moves the anvil member from the open position to the closed position and concomitantly ejects the plurality of surgical fasteners from the cartridge.

13. A self-contained powered surgical apparatus for applying surgical fasteners to body tissue comprising:
a) an elongate body defining a longitudinal axis;
b) a cartridge supported by said elongate body and housing a plurality of surgical fasteners and having a tissue engaging surface thereon;
c) an anvil member having a fastener forming surface thereon, the anvil member mounted adjacent the cartridge and configured for relative movement between an open position wherein said fastener forming surface is spaced from said tissue engaging surface and a closed position wherein said fastener forming surface is in close cooperative alignment with said tissue engaging surface;
d) a motor assembly disposed within the elongate body;
e) a power source disposed within the elongate body for energizing the motor assembly;
f) an actuator for selectively controlling the motor assembly to operate the apparatus;
g) an actuating assembly driven by the motor assembly and mounted for movement in a longitudinal direction to effect relative movement of the anvil member and the cartridge and to effect sequential ejection of a plurality of surgical fasteners from the cartridge; and
h) an elongate extension member configured to engage a proximal end of the elongate body to facilitate utilization of the apparatus during an endoscopic surgical procedure.

14. A powered surgical apparatus as recited in claim 13, wherein the actuating assembly includes a longitudinally translating drive member driven by the motor assembly and first and second camming mechanisms driven by the drive member.

15. A powered surgical apparatus as recited in claim 14, wherein movement of the drive member in a longitudinal direction initially causes the first camming mechanism to effect relative movement of the anvil member and the cartridge and subsequently causes the second camming mechanism to effect sequential ejection of a plurality of surgical fasteners from the cartridge.

16. A powered surgical apparatus as recited in claim 15, wherein the drive member is threadably associated with an axial drive screw which is driven by the motor assembly.

17. A self-contained powered surgical apparatus for applying surgical fasteners to body tissue comprising:
a) an elongate body defining a longitudinal axis and having proximal and distal end portions;
b) a cartridge supported by said elongate body and housing a plurality of surgical fasteners and having a tissue engaging surface thereon;
c) an anvil member having a fastener forming surface thereon, the anvil member mounted adjacent the cartridge, the anvil member and cartridge being relatively movable between a first position wherein said fastener forming surface is spaced from said tissue engaging surface and a second position wherein said fastener forming surface is in close cooperative alignment with said tissue engaging surface;
d) a motor assembly disposed within the elongate body;
e) a power source disposed within the elongate body for energizing the motor assembly, the elongate body having a substantially uniform outer diameter along its entire length, such that said proximal and distal end portions have substantially the same diameter; and
f) an actuating assembly driven by the motor assembly and mounted for movement in a longitudinal direction to effect sequential ejection of a plurality of surgical fasteners from the cartridge.

18. A powered surgical apparatus as recited in claim 17, wherein the actuating assembly includes a longitudinally translating drive member driven by the motor assembly and first and second camming mechanisms driven by the drive member.

19. A powered surgical apparatus as recited in claim 18, wherein movement of the drive member in a longitudinal direction initially causes the first camming mechanism to effect relative movement of the anvil member and the cartridge and subsequently causes the second camming mechanism to effect sequential ejection of a plurality of surgical fasteners from the cartridge.

20. A powered surgical apparatus as recited in claim 19, wherein the drive member is threadably associated with an axial drive screw which is driven by the motor assembly.

21. A powered surgical apparatus as recited in claim 17, wherein the apparatus has an operative length of less than about 7.0 inches.

22. A powered surgical apparatus as recited in claim 17, wherein the outer diameter is between about 0.450 and about 0.500 inches.

* * * * *